(12) United States Patent  (10) Patent No.: US 7,868,045 B2
Ueno  (45) Date of Patent: Jan. 11, 2011

(54) METHOD FOR PROMOTING GASTROINTESTINAL BICARBONATE SECRETION

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 189 days.

(21) Appl. No.: 11/850,271

(22) Filed: Sep. 5, 2007

(65) Prior Publication Data

US 2008/0070979 A1 Mar. 20, 2008

Related U.S. Application Data

(60) Provisional application No. 60/842,382, filed on Sep. 6, 2006.

(51) Int. Cl.
*A61K 31/352* (2006.01)
*A61K 31/19* (2006.01)

(52) U.S. Cl. ..................... 514/573; 514/458

(58) Field of Classification Search ............ None
See application file for complete search history.

(56) References Cited

U.S. PATENT DOCUMENTS

| 5,284,858 A | 2/1994 | Ueno et al. |
| 7,064,148 B2 | 6/2006 | Ueno et al. |

FOREIGN PATENT DOCUMENTS

| EP | 0 160 495 A2 | 11/1985 |
| WO | 2004/060377 A1 | 7/2004 |
| WO | 2006/101244 A2 | 9/2006 |

OTHER PUBLICATIONS

The Merck Index, 17th edition (1999), pp. 221-223.*
Newton, J.L., Mechanisms of Ageing and Development,125 (2004), pp. 867-870.*
Dong et al., American Gastroenterologic Association Abstracts, Supplement 1, 134(4), (Apr. 2008).*
Koji Takeuchi, Hideki Ukawa, Shinichi Kato, Osamu Furukawa, Hideo Araki, Yukihiko Sugimoto, Atsusi Ichikawa, Fumitaka Ushikubi, and Shuh Narumiya; Impaired Duodenal Bicarbonate Secretion and Mucosal Integrity in Mice Lacking Prostaglandin E-receptor Subtype $EP_3$; Gastroenterology 1999;117:1128-1135.
Gunnar Flemstrom et al., Gastroduodenal Mucosal Alkaline Secretion and Mucosal Protection, News Physiol. Sci., Feb. 2001, pp. 23-28, vol. 16.
K. Takeuchi et al., Prostaglandin E Receptor Subtypes Involved in Stimulation of Gastroduodenal Bicarbonate Secretion in Rats and Mice, Journal of Physiology and Pharmacology, 1999, pp. 155-167, vol. 50.
Parimal Bhattacherjee et al., Studies on Receptor Binding and Signal Transduction Pathways of Unoprostone Isopropyl, Journal of Ocular Pharmacology and Therapeutics, 2001, pp. 433-441, vol. 17, No. 5.

* cited by examiner

*Primary Examiner*—Phyllis G. Spivack
(74) *Attorney, Agent, or Firm*—Sughrue Mion, PLLC

(57) ABSTRACT

Provided is a method for promoting bicarbonate secretion in the stomach or duodenum in a mammalian subject, which comprises administering an effective amount of a compound of Formula (I):

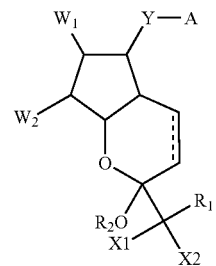

to a subject in need thereof, wherein A, Y, $W_1$, $W_2$, $X_1$, $X_2$ $R_1$ and $R_2$ are herein defined. The compound are also useful for protecting the gastrointestinal tract of a mammal from mucosal damage.

6 Claims, No Drawings

METHOD FOR PROMOTING GASTROINTESTINAL BICARBONATE SECRETION

CROSS-REFERENCE TO RELATED APPLICATION

This application claims the benefit of a previously filed Provisional Application No. 60/842,382 filed Sep. 6, 2006, the whole contents of which is hereby incorporated by reference.

TECHNICAL FIELD

The present invention relates to a method for promoting gastrointestinal bicarbonate secretion in a mammalian subject.

The present invention further relates to a method for protecting the gastrointestinal tract in a mammalian subject from mucosal damage.

BACKGROUND ART

Secretion of bicarbonate provides a mucosal protection at the epithelial surfaces in the gastrointestinal tracts. The mucosa is exposed to noxious agents, including high concentrations of ethanol and medications such as aspirin and other nonsteroidal anti-inflammatory drugs (NSAIDs). In each organ, bicarbonate secretion protects potential mucosal damage induced by acid, pepsin, certain drugs such as NSAIDs, and bacterial infection (News Physiol. Sci. 16, 23-28, 2001, the reference is herein incorporated by reference).

Prostaglandins (hereinafter, referred to as PG(s)) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

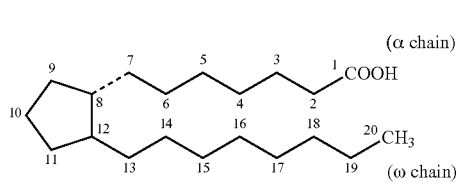

On the other hand, some of synthetic analogues of primary PGs have modified skeletons. The primary PGs are classified into PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety;

Subscript 1: 13,14-unsaturated-15-OH
  Subscript 2: 5,6- and 13,14-diunsaturated-15-OH
  Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

$PGE_1$ and $PGE_2$ and $PGE_3$ are known to have vasodilation, hypotension, gastric secretion decreasing, intestinal tract movement enhancement, uterine contraction, diuretic, bronchodilation and anti ulcer activities. $PGF_1\alpha$, $PGF_2\alpha$ and $PGF_3\alpha$ have been known to have hypertension, vasoconstriction, intestinal tract movement enhancement, uterine contraction, lutein body atrophy and bronchoconstriction activities.

Some 15-keto (i.e., having oxo at the 15-position instead of hydroxy)-PGs and 13,14-dihydro (i.e., having single bond between the 13 and 14-position)-15-keto-PGs are known as the substances naturally produced by the action of enzymes during the metabolism of primary PGs.

U.S. Pat. No. 7,064,148 to Ueno et al. (the reference is herein incorporated by reference) describes that specific prostaglandin compounds including bicyclic tautomer of 15-keto-prostaglandin compounds open and activate chloride channels, especially ClC channels, more especially ClC-2 channel.

Recent findings suggest that PGs stimulate bicarbonate secretion in stomach and duodenum by acting on the PG receptors (J Physiol. Pharmacol. 50(2), 155-167, 1999, the reference is herein incorporated by reference).

On the other hand, it is reported that unoprostone isopropyl, one of the 15-keto-prostaglandin compounds does not have affinity for PG receptors such as EP and FP receptors (Journal of Ocular Pharmacology and Therapeutics 17(5), 433-441, 2001, the reference is herein incorporated by reference).

SUMMARY OF THE INVENTION

The present inventor conducted an intensive study and found that a certain prostaglandin compound promotes the gastrointestinal bicarbonate secretion, thereby it is useful for protecting the gastrointestinal tract from mucosal damage, which have resulted in the completion of the present invention.

Namely, the present invention relates to a method for promoting bicarbonate secretion in the gastrointestinal tract in a mammalian subject, which comprises administering to the subject in need thereof an effective amount of a compound represented by Formula (I) and/or its tautomer:

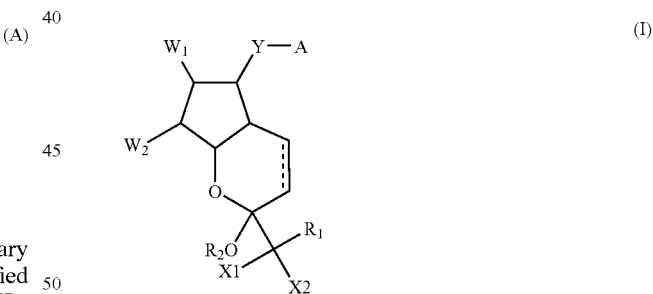

wherein $W_1$ and $W_2$ are

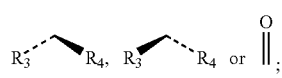

$R_3$ and $R_4$ are hydrogen; or one of them is OH and the other is hydrogen;

$X_1$ and $X_2$ are hydrogen, lower alkyl or halogen, provided that at least one of them is halogen;

$R_2$ is a hydrogen or lower alkyl;

Y is a saturated or unsaturated $C_{2-10}$ hydrocarbon chain, which is unsubstituted or substituted by oxo, halogen, alkyl, hydroxyl or aryl;

A is —CH$_2$OH, —COCH$_2$OH, —COOH or its functional derivative;

R$_1$ is a saturated or unsaturated, straight chain-, branched chain- or ring-forming lower hydrocarbon, which is unsubstituted or substituted by halogens oxo, hydroxy, lower alkyl, lower alkoxy, lower alkanoyloxy, lower cycloalkyl, lower cycloalkyloxy, aryl, or aryloxy; lower cycloalkyl; lower cycloalkyloxy; aryl or aryloxy;

the bond between C-13 and C-14 position is double or single bond, and the steric configuration at C-15 position is R, S, or a Mixture thereof.

The present invention further relates to a method for protecting the gastrointestinal tract from mucosal damage in a mammalian subject, which comprises administering an effective amount of a compound represented by Formula (I) and/or its tautomer to the subject in need thereof.

DETAILED DESCRIPTION OF THE INVENTION

The compound used in the present application is represented by Formula (I):

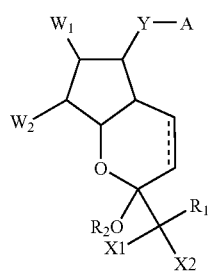

(I)

wherein W$_1$ and W$_2$ are

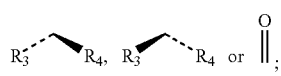

R$_3$ and R$_4$ are hydrogen; or one of them is OH and the other is hydrogen;

X$_1$ and X$_2$ are hydrogen, lower alkyl or halogen, provided that at least one of them is halogen;

R$_2$ is a hydrogen or lower alkyl;

Y is a saturated or unsaturated C$_{2-10}$ hydrocarbon chain, which is unsubstituted or substituted by oxo, halogen, alkyl, hydroxyl or aryl;

A is —CH$_2$OH, —COCH$_2$OH, —COOH or its functional derivative;

R$_1$ is a saturated or unsaturated, straight chain-, branched chain- or ring-forming lower hydrocarbon, which is unsubstituted or substituted by halogen, oxo, hydroxy, lower alkyl, lower alkoxy, lower alkanoyloxy, lower cycloalkyl, lower cycloalkyloxy, aryl, or aryloxy; lower cycloalkyl; lower cycloalkyloxy; aryl or aryloxy;

the bond between C-13 and C-14 position is double or single bond, and the steric configuration at C-15 position is R, S, or a mixture thereof.

In the above formula, the term "halogen" is used to include fluorine, chlorine, bromine, and iodine atoms. Particularly preferable halogen atoms for X$_1$ and X$_2$ are fluorine atoms.

The term "unsaturated" in the definitions for R$_1$ and Y is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower" throughout the specification and claims is intended to include a group having 1 to 6 carbon atoms unless otherwise specified.

The term "ring" refers to lower cycloalkyl, lower cycloalkyloxy, aryl or aryloxy.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkoxy" refers to a group of lower alkyl-O—, wherein lower alkyl is as defined above.

The term "lower alkanoyloxy" refers to a group represented by the formula RCO—O—, wherein RCO— is an acyl group formed by oxidation of a lower alkyl group as defined above, such as acetyl.

The term "lower cycloalkyl" refers to a cyclic group formed by cyclization of a lower alkyl group as defined above but contains three or more carbon atoms, and includes, for example, cyclopropyl, cyclobutyl, cyclopentyl and cyclohexyl.

The term "lower cycloalkyloxy" refers to the group of lower cycloalkyl-O—, wherein lower cycloalkyl is as defined above.

The term "aryl" refers to unsubstituted or substituted aromatic carbocyclic or heterocyclic groups, preferably monocyclic groups, for example, phenyl, naphthyl, tolyl, xylyl, furyl, thienyl, pyrrolyl, oxazolyl, isoxazolyl, thiazolyl, isothiazolyl, imidazolyl, pyrazolyl, furzanyl, pyranyl, pyridyl, pyridazyl, pyrimidryl, pyrazyl, pyrrolidinyl, imidazolidinyl, pyrazolidinyl, piperidino, piperazinyl, morpholono, indolyl, benzothienyl, quinolyl, isoquinolyl, puryl, quinazolinyl, carbazolyl, acridinyl, phenathridinyl, benzimidazolyl, benzimidazolonyl, benzothiazolyl and phenothiazinyl. Examples of substituents are halogen atom and halo (lower)alkyl, wherein halogen atom and lower alkyl are as defined above.

The term "aryloxy" refers to a group represented by the formula ArO—, wherein Ar is aryl as defined above.

The term "functional derivative" of A includes salts, preferably pharmaceutically acceptable salts, ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy(lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A means a group represented by the formula —CONR'R", wherein each of R' and R" is hydrogen, lower alkyl, aryl, alkyl- or aryl-sulfonyl, lower alkenyl and lower alkynyl, and includes for example, lower alkyl amides such as methylamide, ethylamide, dimethylamide and diethylamide; arylamides such as anilide and toluidide; and alkyl- or aryl-sulfonylamides such as methylsulfonylamide, ethylsulfonylamide and tolylsulfonylamide.

Examples of Y include, for example, the following groups:
—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$—CH=CH—,
—$CH_2$—C≡C—$CH_2$—$CH_2$—$CH_2$—,
—$CH_2$—$CH_2$—$CH_2$—$CH_2$—O—$CH_2$—,
—$CH_2$—CH=CH—$CH_2$O—$CH_2$—,
—$CH_2$—C≡C—$CH_2$—O—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—,
—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—$CH_2$—CH($CH_3$)—$CH_2$—,
—$CH_2$—$CH_2$—$CH_2$—$CH_2$—CH($CH_3$)—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—$CH_2$—, and
—$CH_2$—$CH_2$—$CH_2$—$CH_2$—$CH_2$—$CH_2$—CH($CH_3$)—$CH_2$—.

Further, at least one carbon atom in the aliphatic hydrocarbon of Y is optionally substituted by oxygen, nitrogen or sulfur.

Preferred A is —COOH or its pharmaceutically acceptable salt or ester.

Preferred $X_1$ and $X_2$ are both being halogen atoms, and more preferably, fluorine atoms.

Preferred $W_1$ is =O.

Preferred $W_2$ is

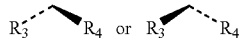

where $R_3$ and $R_4$ are both hydrogen atoms.

Preferred Y is an unsubstituted saturated or unsaturated hydrocarbon chain having 6-8 carbon atoms.

Preferred $R_1$ is a hydrocarbon containing 1-6 carbon atoms, more preferably, 1-4 carbon atoms. $R_1$ may have one or two side chains having one carbon atom.

$R_2$ is preferably hydrogen.

Most preferred embodiment is a prostaglandin compound of Formula (I) in which A is —COOH; Y is $(CH_2)_6$; $W_1$ is =O; $W_2$ is

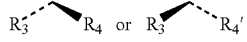

wherein $R_3$ and $R_4$ are both hydrogen atoms; $R_2$ is hydrogen atom; $X_1$ and $X_2$ are fluorine; and $R_1$ is $(CH_2)_3 CH_3$ or $CH_2 CH(CH_3)CH_2CH_3$.

The compound of Formula (I) used in the present invention exists as a bicyclic compound in a solid state, but in a solvent, a part of the compound may be in the form of the mono-cyclic tautomer. In the absence of water, the compound represented by Formula (I) exists predominantly in the form of the bicyclic structure. In aqueous media, some parts of the compound may become in the form of its monocyclic tautomer. It is believed that hydrogen bonding occurs between, for example, the ketone position at the C-15 position, thereby hindering bicyclic ring formation. In addition, it is believed that the halogen atoms at the C-16 position promote bicyclic ring formation. The tautomerism between the hydroxy at the C-11 position and the keto moiety at the C-15 position, shown below, is especially significant in the case of compounds having a 13,14 single bond and two fluorine atoms the C-16 position.

Accordingly, in the specification and claims, a compound of Formula (I) represented as the bicyclic form also covers its mono-cyclic tautomer. For example, bicyclic and monocyclic forms of a compound having a keto group at the C-15 position and halogen atoms at the C-16 position may be as follows.

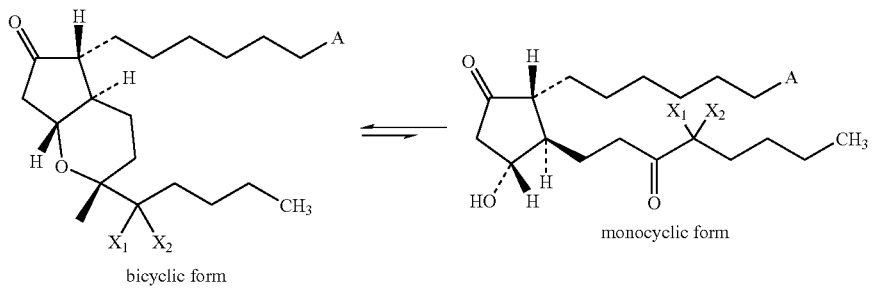

bicyclic form ⇌ monocyclic form

Further, while the compounds used in the invention may be represented by a name based on the mono-cyclic tautomer regardless of the presence or absence of the isomers, it is to be noted that such structure or name does not intend to exclude the bicyclic type compound.

A preferred compound according to the invention in its monocyclic form can be named as 13,14-dihydro-15-keto-16,16-difluoro-$PGE_1$ or 13,14-dihydro-15-keto-16,16-difluoro-18(S)-methyl-$PGE_1$, according to conventional prostaglandin nomenclature.

The compound used in the present invention may be prepared by the method disclosed in U.S. Pat. No. 5,284,858 and U.S. Pat. No. 5,739,161 (these cited references are herein incorporated by reference).

According to the present invention, the subject to be treated may be any mammalian subject including a human. The compound of Formula (I) may be applied systemically or topically. Usually, the compound may be administered by oral administration, intranasal administration, inhalational administration, intravenous injection (including infusion), subcutaneous injection, intra rectal administration, transdermal administration and the like.

The dose may vary depending on the strain of the animal, age, body weight, symptom to be treated, desired therapeutic effect, administration route, term of treatment and the like. A satisfactory effect can be obtained by systemic or topical administration 1-4 times per day or continuous administration at the amount of 0.00001-500 µg/kg per day, preferably 0.0001-100 µg/kg, more preferably 0.001-10 µg/kg.

The compound of Formula (I) may preferably be formulated in a pharmaceutical composition suitable for administration in a conventional manner. The composition may be those suitable for oral administration, intranasal administration, inhalational administration, injection or perfusion as well as it may be an external agent, suppository or pessary.

The composition of the present invention may further contain physiologically acceptable additives. Said additives may include the ingredients used with the present compounds such as excipient, diluent, filler, resolvent, lubricant, adjuvant, binder, disintegrator, coating agent, capsulating agent, ointment base, suppository base, aerozoling agent, emulsifier, dispersing agent, suspending agents thickener, tonicity agent, buffering agent, soothing agent, preservative, antioxidant, corrigent, flavor, colorant, a functional material such as cyclodextrin and biodegradable polymer, stabilizer. The additives are well known to the art and may be selected from those described in general reference books of pharmaceutics.

The amount of the above-defined compound in the composition of the invention may vary depending on the formulation of the composition, and may generally be 0.000001-10.0%, more preferably 0.00001-5.0%, most preferably 0.0001-1%.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary. They may be covered with two or more layers. They may also be adsorbed to a sustained release material, or microcapsulated. Additionally, the compositions may be capsulated by means of an easily degradable material such gelatin. They may be further dissolved in an appropriate solvent such as fatty acid or its mono, di or triglyceride to be a soft capsule. Sublingual tablet may be used in need of fast-acting property.

Examples of liquid compositions for oral administration, intranasal administration or inhalational administration include emulsions, solutions, suspensions, syrups and elixirs and the like. Said composition may further contain a conventionally used inactive diluents e.g. purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition, which contains one or more active ingredients and may be prepared according to a known method.

Intranasal preparations may be administered as aqueous or oily solutions, suspensions or emulsions. For the administration of an active ingredient by inhalation, it can be administered in the form of a suspension, solution or emulsion which is present as dry powder or as aerosol, it being possible to use all customary propellants.

Examples of the injectable compositions of the present invention for parenteral administration include sterile aqueous or non-aqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

Another form of the present invention is suppository or pessary, which may be prepared by mixing active ingredients into a conventional base such as cacao butter that softens at body temperature, and nonionic surfactants having suitable softening temperatures may be used to improve absorbability.

As mentioned above, the compound of Formula (I) promotes gastrointestinal bicarbonate secretion, thereby it is useful for protecting the gastrointestinal tracts from mucosal damage induced by acid, pepsin, certain drugs such as NSAIDs and bacterial infection.

The term "gastrointestinal tract" used in the instant specification and claims includes upper gastrointestinal tracts such as esophagus, stomach, duodenum and lower gastrointestinal tracts such as small intestine including jejunum and ileum, and large intestine including colon and rectum. Especially the compound of Formula (I) promotes the bicarbonate secretion in the upper gastrointestinal tracts.

The pharmaceutical composition of the present invention may further contain other pharmacological ingredients as far as they do not contradict the purpose of the present invention.

Further details of the present invention will follow with reference to test examples, which, however, are not intended to limit the present invention.

EXAMPLE

The effect of Compound A (13,14-dihydro-15-keto-16,16-difluoro-18(S)-methyl-PGE$_1$) on Gastrointestinal bicarbonate secretion was studied.

Seven weeks old male Wistar rats were used in this study. Compound A at a dose of 100 µg/kg was administered orally to the animals three times daily for 7 days. Control animals received an equal volume of the vehicle (distilled water containing 0.01% polysorbate 80 and 0.5% ethanol). On the next morning of the final administration (about 17 hours after the final administration), a polyethylene catheter (PE10, Becton Dickinson and Company) was inserted into the common bile duct of the animal under ether anesthesia. The animals were placed into a Borrmann's cage individually and allowed to recover from the anesthesia for 1 hour. Bile was collected for 1 hour between 1 and 2 hours after inserting the catheter. The amount of bicarbonate ($HCO_3^-$) in the bile was measured with an automated pH/blood gas analyzer (model 170, Ciba Corning Diagnostics Corp.).

In the Compound A group, the amount of bicarbonate secreted into the bile was increased significantly as compared with that of the control group.

TABLE 1

Effect of Compound A on bicarbonate secretion

| Group | Dose µg/kg (p.o.), TID for 7 days | n | Bicarbonate secretion µmol/hr/100 g body weight Mean ± S.E. |
|---|---|---|---|
| Control | — | 6 | 10.16 ± 0.81 |
| Compound A | 100 | 7 | 13.33 ± 1.00* |

*p < 0.05 compared with control group (Student's t-test)

The result indicates that the compound of Formula (I) promotes bicarbonates secretion in the gastrointestinal tracts, thereby has protective action on the gastrointestinal tracts from the mucosal damage.

While the invention has been described in detail and with reference to specific embodiments thereof, it will be apparent to one skilled in the art that various changes and modifications can be made therein without departing from the spirit and scope thereof.

What is claimed is:

1. A method for protecting the upper gastrointestinal tract from mucosal damage in a mammalian subject in need thereof, which comprises administering to the subject an effective amount of a compound selected from the group consisting of 13,14-dihydro-15-keto-16,16-difluoro-PGE1; 13,14-dihydro-15-keto-16,16-difluoro-18(S)-methyl-PGE1; a salt, ether, ester or amide thereof; a tautomer thereof and a mixture thereof, wherein bicarbonate secretion is promoted in the upper gastrointestinal tract of the subject so that the upper gastrointestinal tract is protected from mucosal damage, wherein the upper gastrointestinal tract is the stomach and/or duodenum.

2. The method as described in claim 1, wherein the mucosal damage is induced by acid.

3. The method as described in claim 1, wherein the mucosal damage is induced by pepsin.

4. The method as described in claim 1, wherein the mucosal damage is induced by nonsteroidal anti-inflammatory drugs.

5. The method as described in claim 1, wherein the mucosal damage is induced by bacterial infection.

6. A method for promoting bicarbonate secretion in the upper gastrointestinal tract in a mammalian subject, which comprises administering to the subject in need thereof an effective amount of a compound selected from the group consisting of: 13,14-dihydro-15-keto-16,16-difluoro-PGE1; 13,14-dihydro-15-keto-16,16-difluoro-18(S)-methyl-PGE1; a salt, ether, ester or amide thereof, a tautomer thereof and a mixture thereof, wherein the upper gastrointestinal tract is the stomach and/or duodenum.

* * * * *